United States Patent [19]
Haber et al.

[11] Patent Number: 5,417,705
[45] Date of Patent: May 23, 1995

[54] OBTURATOR WITH ROTATING, RESETTABLE SAFETY SHIELD

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 76,342

[22] Filed: Jun. 11, 1993

Related U.S. Application Data

[63] Continuation-in-part of Ser. No. 60,909, May 14, 1993, abandoned.

[51] Int. Cl.⁶ ............................................. A61B 17/34
[52] U.S. Cl. ...................................... 606/185; 604/164
[58] Field of Search ................ 606/185; 604/164, 165, 604/264, 272

[56] References Cited

U.S. PATENT DOCUMENTS

| | | |
|---|---|---|
| 3,994,287 | 11/1976 | Turp et al. . |
| 4,177,814 | 12/1979 | Knepshield et al. . |
| 4,430,081 | 2/1984 | Timmermans ...................... 604/256 |
| 4,610,665 | 9/1986 | Matsumoto et al. ................. 604/167 |
| 4,623,343 | 11/1986 | Thompson . |
| 4,654,030 | 3/1987 | Moll et al. . |
| 4,902,280 | 2/1990 | Lander . |
| 4,931,042 | 6/1990 | Holmes et al. . |
| 5,041,095 | 8/1991 | Littrell ............................... 604/167 |
| 5,053,016 | 10/1991 | Lander . |
| 5,057,084 | 10/1991 | Ensminger et al. ................. 604/167 |
| 5,066,288 | 11/1991 | Deniega et al. . |
| 5,098,405 | 3/1992 | Peterson et al. . |
| 5,104,383 | 4/1992 | Shichman . |
| 5,127,626 | 7/1992 | Hilal et al. . |
| 5,141,498 | 8/1992 | Christian . |
| 5,167,636 | 12/1992 | Clement . |
| 5,197,955 | 3/1993 | Stephens et al. . |
| 5,226,426 | 7/1993 | Yoon ............................... 604/164 X |

FOREIGN PATENT DOCUMENTS

| | | | |
|---|---|---|---|
| 4116648A1 | 11/1992 | Germany ...................... | A61B 17/34 |
| WO91/17781 | 11/1991 | WIPO ........................... | A61M 5/178 |

*Primary Examiner*—Michael H. Thaler
*Attorney, Agent, or Firm*—Townsend and Townsend Khourie and Crew

[57] ABSTRACT

An obturator (2) includes a hollow housing (4) with an obturator barrel (6) extending therefrom. The tip (172) of the obturator has a cutting element (40) and a safety shield (46). The safety shield is automatically rotatable from a cutting position, with the blade exposed, to a safe position, with the blade shielded, when the blade has passed through the tissue layer being pierced. The safety shield can be returned to the cutting position using a rearming device (128, 274) mounted to the housing at the proximal end of the obturator. The obturator barrel (6a) can be bent for use.

51 Claims, 14 Drawing Sheets

OBTURATOR WITH ROTATING, RESETTABLE SAFETY SHIELD

Cross Reference to Related Applications

This is a continuation-in-part of U.S. patent application No. 08/060,909, filed May 14, 1993, now abandoned, for OBTURATOR WITH ROTATING, RESETTABLE SAFETY SHIELD, the disclosure of which is incorporated by reference.

This is also related to U.S. patent application Ser. No. 08/015,170, filed Feb. 9, 1993 for TROCAR; U.S. patent application Ser. No. 08/019,548, filed Feb. 19, 1993, now U.S. Pat. No. 5,354,280, for TROCAR AND SEAL; U.S. patent application Ser. No. 08/031,174, filed Mar. 11, 1993, now U.S. Pat. No. 5,385,552, for TROCAR WITH OVERLAPPING SEAL ELEMENTS; U.S. patent application Ser. No. 08/033,315 filed Mar. 15, 1993, now abanboned, for TROCAR WITH IMPROVED OBTURATOR; and U.S. patent application Ser. No. 08/039,910 filed Mar. 30, 1993, now U.S. Pat. No. 5,366,745, for TROCAR WITH ROTATING SAFETY SHIELD, the disclosures of which are incorporated by reference.

BACKGROUND OF THE INVENTION

Practitioners of medicine or surgery frequently advise a patient to undergo an invasive procedure for either diagnostic or therapeutic reasons. One such invasive procedure involves the use of a trocar which includes an obturator, having a sharpened end for piercing the wall of a body cavity, and a trocar body, through while the obturator passes. The trocar body, after being removed of the obturator, is used to guide an endoscopic instrument into the body cavity. The trocar body minimizes traumatization to the tissue from the endoscopic instrument, stabilizes such endoscopic instrument, and provides a seal for insufflation of gasses to expand the operating theater. Thus, the practitioner can gain access to the cavity to withdraw a substance such as a fluid or biopsy specimen and to introduce a gas such as carbon dioxide or an instrument, such as a surgical tool. A laparoscope, a flexible fiberoptic endoscope, is an example of a surgical instrument often introduced through the trocar body. The trocar body also helps to avoid trauma to the tissue surrounding the opening while inserting and withdrawing a surgical instrument.

Any of the numerous body cavities can be accessible to trocar invasion. Sites for introduction of a trocar include the abdomen and the pelvis. A laparoscope can be introduced through the trocar body for visualization, biopsy, and certain surgical procedures. Other body cavities which commonly benefit from endoscopic procedure include the thoracic, cranial, and various joint cavities.

A general technique for introduction of a trocar includes induction of appropriate anesthesia which may be general, local or a combination of both. The area to be pierced by the trocar, such as the skin of the abdomen, is prepped and cleansed conventionally. Typically, the operator makes a nick or a small skin incision with a scalpel blade. The sharpened tip of the conventional trocar is introduced through the nick or incision, and the conventional trocar is pushed downward to and through the fatty tissue. The conventional trocar is further pushed so that its sharpened tip pierces the muscular fascial layer to enter the abdominal cavity.

In the case of laparoscopic surgery (surgery inferior to the diaphragm) a biocompatible gas such as carbon dioxide ($CO_2$) is introduced under pressure into the abdominal cavity to create a space between the muscular fascial layer of the inner abdominal wall and the vital organs posterior to this wall. Such vital organs in the abdomen include the bowel (large and small intestine), the liver, stomach and other structures. Use of $CO_2$ insufflation of the pelvic region tends to protect the bladder and the reproductive organs as well as their associated vascular structures from inadvertent puncture by the sharpened trocar. This is so because of the increased separation between the organs resulting from the expansion of the abdominal cavity due to internal $CO_2$ gas pressure.

A problem attendant to using a sharp tipped trocar in body cavities is the possibility of accidentally piercing or disturbing tissue not intended to be violated. Typically, such tissue is deep to the wall covering the cavity. For example, puncture of the bowel is a complication of trocar use in the abdominal cavity. Complications from inadvertent puncture with the trocar can range from minor to serious. For instance, nicking the uterus with a trocar during a pelvic laparoscopy may be a minor event requiring no therapeutic reaction. Nicking an artery such as the ovarian artery, however, would require immediate surgical repair. Repair may not be possible through a laparoscope but may instead require an open procedure. Similarly, accidental nicking of the intestine could require immediate surgical repair.

Even if repair is undertaken aggressively, complications may ensue. For example, loss of blood from a severed artery could require a transfusion and could result in morbidity or mortality. Similarly, a pierced bowel, although promptly treated, may result in abdominal complications including peritonitis, which is an acute inflammatory condition. Other complications can include abdominal infection which, if it goes undetected, can result in abscess formation or subsequent peritonitis. These conditions can be fatal.

The inadvertent puncture of a structure while placing a sharpened trocar can occur in part because the operator is pushing against the abdominal wall inwardly as the trocar is introduced. This action tends to decrease the space between the internal aspect of the abdominal wall and vital structures such as the bowel. In any event, the essential problem is that the trocar is advanced too deeply through and beyond the abdominal fascia and cuts into a vital structure accidentally.

One approach to help solve this problem has been the use of auto sheathing. Auto sheathing means that the trocar includes a means for detecting absence of resistance. When this absence of resistance is encountered, the automatic sheathing device is activated and moves axially to cover or protect the sharpened trocar tip. Typically, this decrease or absence of resistance occurs after puncture of the inner fascial layer and as the trocar tip enters the cavity such as the abdominal cavity which offers minimal or essentially no resistance. Because a vital structure may be very close to the trocar tip shortly after the trocar tip is admitted to the cavity, the time frame for automatic sheathing to act is very narrow.

An additional complication of using the conventional trocar is that the sharpened tip causes a puncturing or incisional pattern in the shape of a Y or other nonlinear pattern. This pattern is not under the control of the operator, but rather is a feature of the device itself. Such a jagged incision tends to heal less rapidly than a simple linear incision. Additionally, in certain tissues such as muscle, a linear incision parallel to the tissue fiber planes permits more rapid healing. In contrast, a cut across the grain of the muscle fiber can prolong the healing process as well as weaken the muscle permanently due to increased formation of granular tissue.

SUMMARY OF THE INVENTION

The present invention is directed to an obturator usable with a hollow trocar body. The obturator has a pivotal safety shield at the obturator's tip. The safety shield is pivotally mounted to the tip of the obturator for movement between a cutting position, at which the cutting element is exposed, and a safe position, at which the cutting element is covered by the safety shield. This movement occurs automatically with passage of the cutting element at least partly through the tissue layer being cut. The safety shield can be returned to the cutting position, so to re-expose the cutting element, by manipulation of a rearming device at the proximal end of the obturator.

In the preferred embodiments the safety shield, which is normally biased from the cutting position to the safe position by a drive spring, is maintained in the cutting position until a release button at the tip of the obturator is depressed. The release button is positioned so that the cut tissue depresses the release button to permit the safety shield to pivot, under the influence of the spring, from the cutting position to the safe position.

The safety shield, in one preferred embodiment, includes a pulley integrally formed with the safety shield. The pulley is connected to the distal ends of a pair of drive cable segments. The proximal end of one cable segment is placed in tension by the drive spring while the proximal end of the other cable segment is connected to a safety shield control element. The drive spring pulls on the one cable segment to bias the safety shield from the cutting position to the safe position. The safety shield control element is a user operable element and is used to pull on the other cable segment to return the safety shield to the cutting position.

The safety shield, in a second preferred embodiment, includes an integral pulley configured so that the drive cable segments each wrap around the pulley so that neither of the cable segments ever unwinds completely from the pulley. This is important since the cable is typically severely bent or crimped adjacent where they are joined to one another and to the pulley. Therefore the bent or crimped regions are not flexed or worked during use so that work hardening, and the resulting failure of the drive cable at those points, is eliminated. The specific configuration of the pulley and the method by which the cable is pre-bent and mounted to the pulley enhances the ease of assembly as well.

The pivot point of the safety shield when in the cutting position is, in the preferred embodiment, forward or distal of the center of the safety shield. This helps to ensure the safety shield remains in or close to the cutting position during the initial cutting of the tissue layer since the cut tissue keeps the safety shield from pivoting to the safe position. Only after the tip of the obturator is at least substantially through the tissue layer can the safety shield pivot around its own axis to the safe position. This occurs automatically and very quickly after the tip of the obturator has passed fully or partially through the tissue layer to help prevent inadvertent injury to structures internal of the tissue layer being cut.

An advantage of the invention relates to the type of incision made by the invention. A simple, linear incision may permit the wound to heal much more quickly than the multilobed puncture wound created by a conventional obturator. Also, the surgeon can orient the direction of the cut created by the present invention so that the cut is made parallel to tissue fiber planes to promote rapid healing. An indicating line denoting orientation of the plane of the cutting blade permits rotational alignment of the cutting blade and plane to be made parallel to muscle fibers direction for minimum trauma and minimum healing time. This is not possible when using conventional obturators. Another advantage arises from the ability of the user to reset the safety shield to the cutting position from the proximal end of the obturator.

An alternative embodiment of the invention provides an obturator barrel which is flexible. The obturator barrel can be of the type which is pre-flexed to a desired curvature. Alternatively, the obturator barrel can be remotely guided in a manner similar to endoscopic instruments. In addition, the cutting edge of the blade can be provided with a conventional smooth, scalpel type edge or with a scalloped, saw tooth, serrated or other irregular edge. It has been found that certain tissues are best cut using smooth, scalpel type edges while other tissues are best cut using irregular edges.

Other features and advantages of the invention will appear from the following description in which the preferred embodiments have been set forth in detail in conjunction with the accompanying drawings.

DESCRIPTION OF THE PREFERRED EMBODIMENTS

Figure 1:
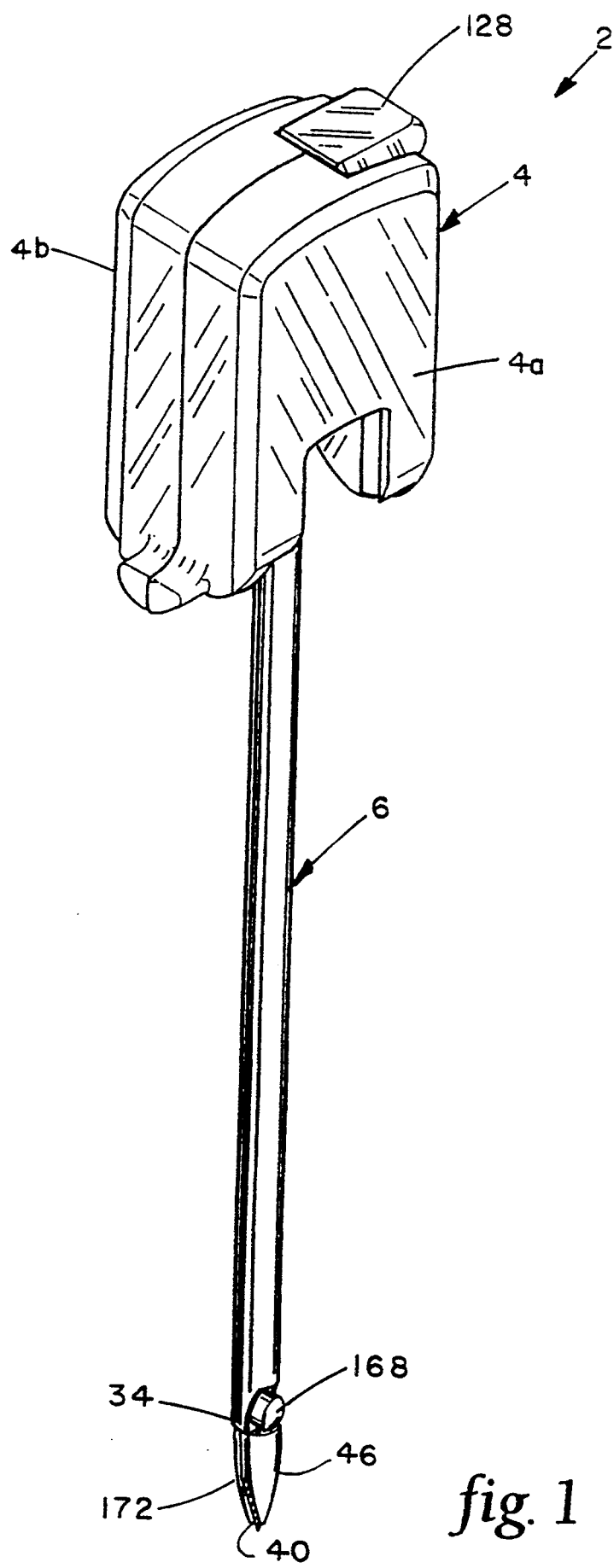
FIG. 1 is an overall isometric view of an obturator made according to the invention.
Figure 2:
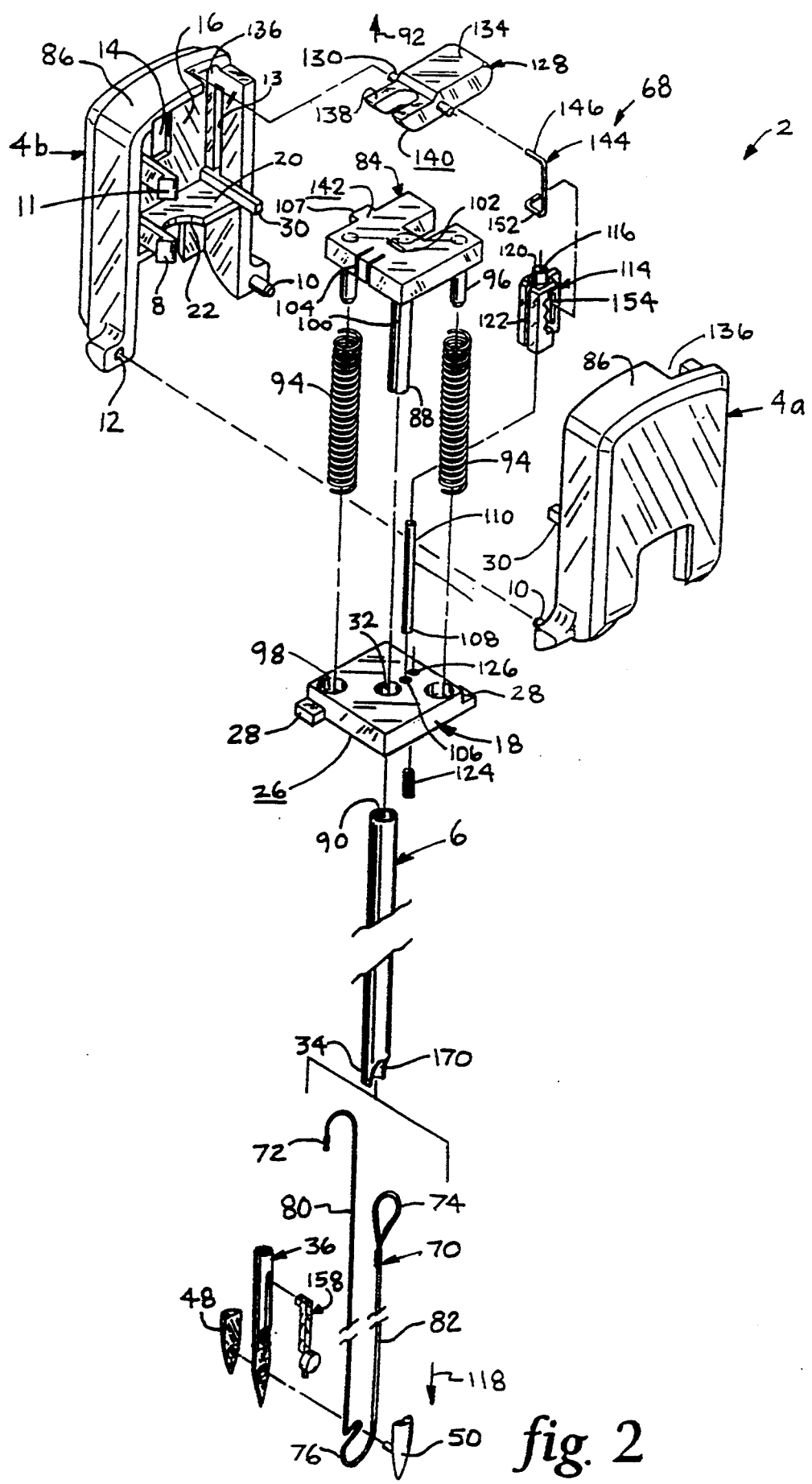
FIG. 2 is an exploded isometric view of the obturator of FIG. 1.

FIGS. 1 and 2 illustrate an obturator 2 of the type used with the trocar body, not shown. Obturator 2 includes a housing 4 from which obturator barrel 6 extends. Housing 4 includes housing halves 4a, 4b which are secured to one another using clip arms 8, pins 10 and complementary pin openings 12. Housing halves 4a, 4b are substantially mirror images of one another with one exception. Housing half 4b has a rectangular opening 14 formed in its outer face 16 of housing half 4b. The use of opening 14 will be discussed below. The distal ends 11 of clip arms 8 of one housing half 4a, 4b engage grooves 13 formed in the other housing half 4b, 4a.

Figure 3A:
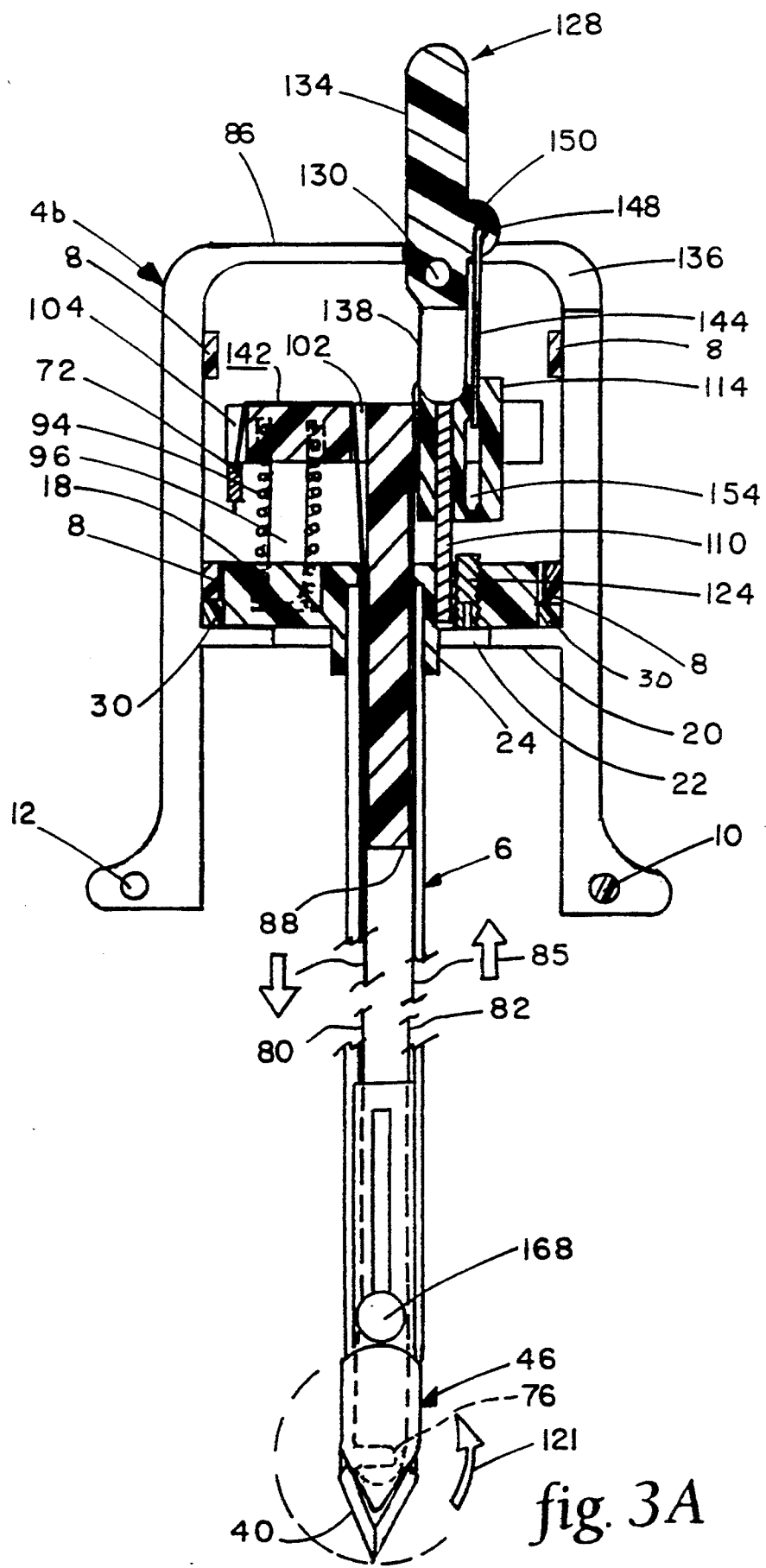
FIGS. 3A and 3B are enlarged simplified cross-sectional views of the obturator of FIG. 2 immediately following moving the rearming lever to return the safety shield to the cutting position of FIG. 1 and after depression of the actuation button to drive the safety shield to a safe position shielding the cutting element.

A generally rectangular mount plate 18 is supported within housing 4 by bulkhead halves 20. Each bulkhead half 20 has a cut-out 22 which accepts a circular lug 24 extending from the distal surface 26 of mount plate 18 as shown in FIG. 3A. Mount plate 18 has a pair of mounting ears 28 at opposite corners sized to fit beneath the distal-most clip arms 8 adjacent bulkhead halves 20. Housing halves 4a, 4b also include spacer bars 30 which extend beneath the distal-most clip arms 8 of the other housing half 4b, 4a. Spacer bars 30 are sized so that they lie adjacent mounting ears 28 to help maintain mount plate 18 in position.

Figure 2A:
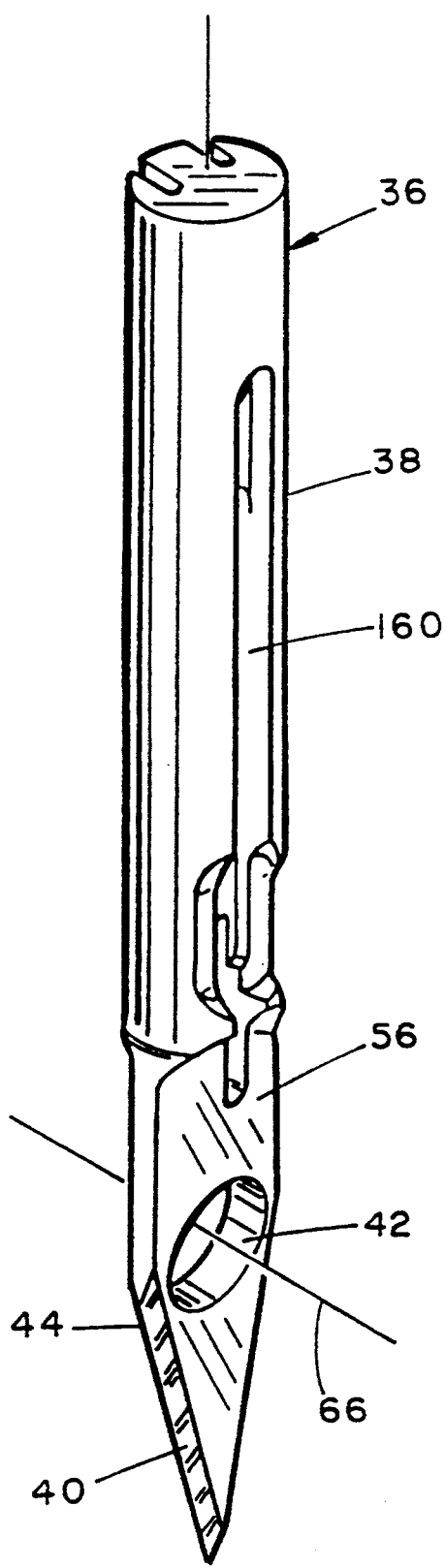
FIGS. 2A and 2B are enlarged isometric views of the blade of FIG. 2.
Figure 2B:
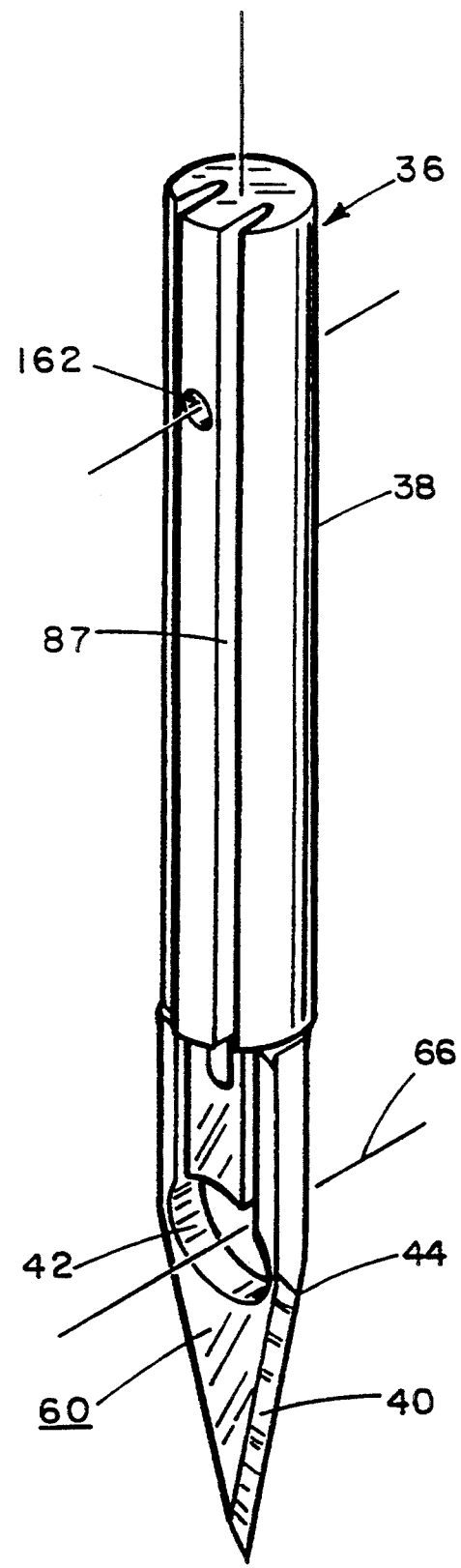

Obturator barrel 6 is preferably made of stainless steel and is press fit into a stepped central opening 32 formed in mount plate 18. Obturator barrel 6 is about 5 mm in diameter in the preferred embodiment. Other diameter obturator barrels can be used as well. Barrel 6 has a distal end 34 within which a blade 36 is mounted. Blade 36, shown in more detail in FIGS. 2A and 2B, is made of stainless steel and has a generally circular shank 38 sized to be rigidly secured to distal end 34 of obturator barrel 6 through a slight interference fit. Blade 36 has a generally V-shaped cutting edge 40 which extends beyond distal end 34 of obturator barrel 6. Blade 36 includes a large opening 42 formed adjacent the proximal end 44 of edge 40. Opening 42 is used to rotatably mount a safety shield 46 to blade 36.

Figure 2D:
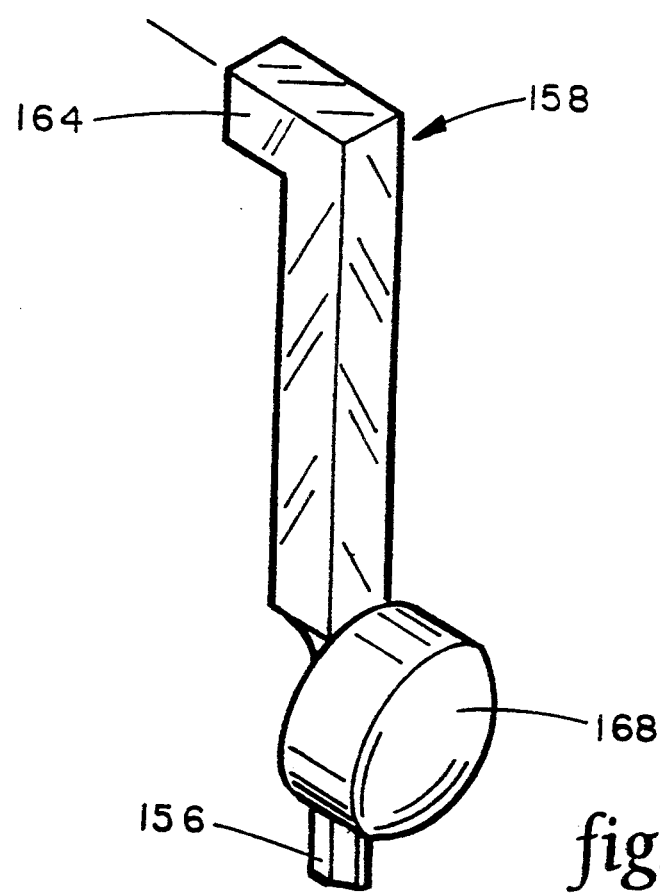
FIG. 2D is an enlarged isometric view of the release spring of FIG. 2.
Figure 2C:
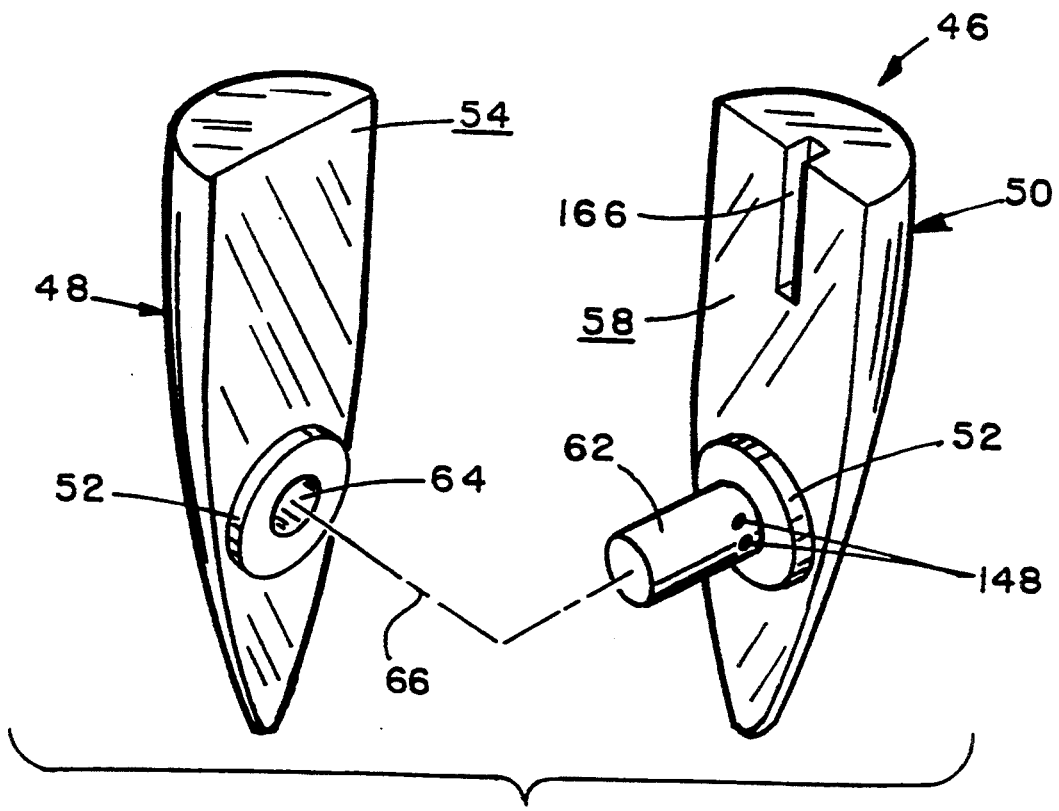
FIG. 2C is an enlarged exploded isometric view of the safety shield of FIG. 2.

Safety shield 46 includes safety shield halves 48, 50 shown best in FIG. 2C. Each safety shield half 48, 50 has a circular boss 52 extending from its inner surface 54. Inner surface 54 of half 48 lies against one surface 56 of blade 36 shown in FIG. 2a. Safety shield half 50 includes an inner surface 58 which lies against another surface 60 of blade 36 shown in FIG. 2B. Bosses 52 each extend about one-third of the way through opening 42. Safety shield half 50 includes a pulley 62 extending from inner surface 58 and into a complementary hole 64 formed in safety shield half 48. Pulley 62 and hole 64 are press fit to one another so that safety shield 46 rotates as a unit about an axis 66.

Figure 3B:
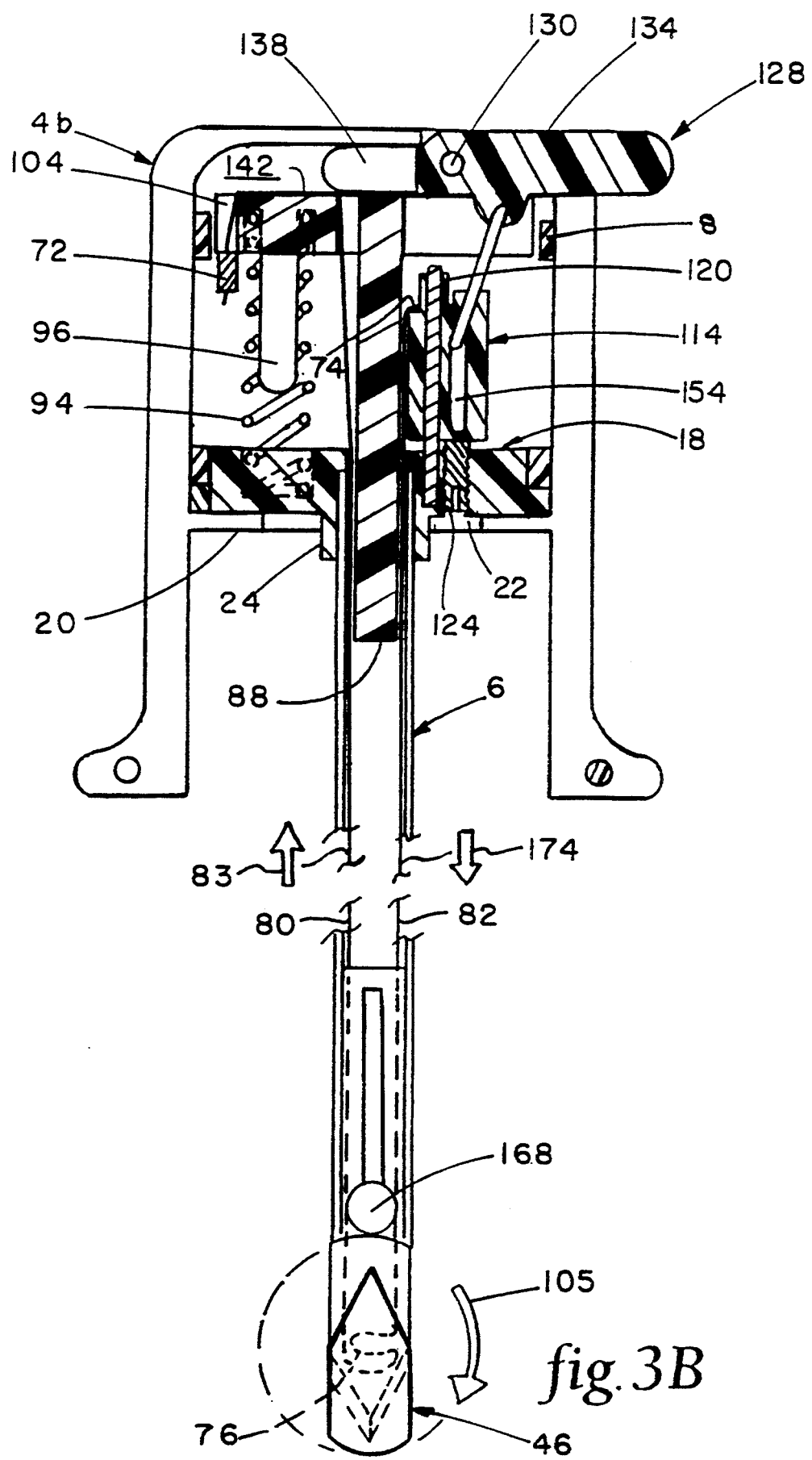

Safety shield 46 is rotated between the cutting position of FIGS. 1 and 3A, with cutting edge 40 exposed, and a safe position, shown in FIG. 3B, with the cutting edge covered or shielded. This is accomplished using a safety shield driving assembly 68 as discussed below. Driving assembly 68 includes a drive cable 70 having first and second proximal ends 72, 74. The intermediate portion 76 of drive cable 70 is threaded through a pair of holes 78 formed in pulley 62 so that pulling on the first cable segment 80, which connects first proximal end 72 of drive cable 70 with intermediate portion 76, causes safety shield 46 to rotate from its cutting position of FIGS. 1 to its safe position of FIG. 3B. This is indicated by arrow 83 of FIG. 3B. Pulling on the second cable segment, coupling second proximal end 74 with intermediate portion 76, see arrow 85 of FIG. 3A, rotates safety shield 46 from the safe position of FIG. 3B back to the cutting position of FIGS. 1 and 3A.

Cable segments 80, 82 extend along a pair axially extending grooves 87 formed in blade 36 and then up through obturator barrel 6.

Safety shield driving assembly 68 includes a generally rectangular drive plate 84 housed within housing 4 between mount plate 18 and the tops 86 of housing halves 4a, 4b. Drive plate 84 has a slotted guide rod 88 which slidably engages the interior 90 of obturator barrel 6. Drive plate 84 is biased in a proximal direction 92 by a pair of drive springs 94 which fit over distally extending guide pegs 96 extending from drive plate 84 at one end and within blind holes 98 formed in mount plate 18. First and second cable segments 80, 82 pass from interior 90 of obturator barrel 6 and along axially extending slots 100 formed on either side of guide rod 88. First proximal end 72 then passes through a slot 102 formed through drive plate 84 and then captured within a narrow slit 104. See FIG. 3A. The enlarged end at first proximal end 72 is too large to pass through narrow slit 104 so that movement of drive plate 84 in proximal direction 92 pulls on first cable segment 80 in the direction of arrow 83 of FIG. 3B to rotate safety shield 46 in the direction of arrow 105 so to move the safety shield from the cutting position to the safe position.

Drive plate 84 has an indicator tab 107 which is housed within opening 14. The position of indicator tab 107 within opening 14 shows whether safety shield 46 is in its safe or cutting positions.

Mount plate 18 has a smaller diameter blind hole 106 sized to accept the distal end 108 of a guide pin 110. Guide pin 110 and blind hole 106 are sized so that guide pin is rigidly secured within hole 106.

Obturator 2 also includes a safety shield returning assembly 112 used to return safety shield 46 from the safe position of FIG. 3B to the cutting position of FIGS. 1 and 3A. Assembly 112 includes a shield control block 114, shown in more detail in FIG. 3B. Shield control block 114 has an axially extending hole 116 to allow block 114 to move freely axially, that is in proximal direction 92 and distal direction 118, along guide pin 110. Block 114 has a proximally extending peg 120 and an axially extending slot 122. Peg 120 acts as a mounting post for the looped end 74 of second cable segment 82 while slot 122 permits looped end 74 to be housed therein and help keep the looped end from being disengaged from peg 120.

As shown in FIG. 3B, shield control block 114 is adjacent mount plate 18 when safety shield 46 is in the safe position. Moving shield control block 114 in proximal direction 92, discussed below, pulls on second cable segment 82 in the direction of arrow 85 thus moving safety shield 46 in the direction of arrow 121 of FIG. 3A from the safe position of FIG. 3B to the cutting position of FIGS. 1 and 3A. The position of control block 114 adjacent mount plate 18 can be adjusted using a set screw 124 which is housed within a threaded hole 126 in mount plate 18. Hole 126 is positioned to lie beneath shield control block 114 and so that set screw 124 acts as an adjustable stop for the shield control block when moving in distal direction 118.

Block 118 is moved in proximal direction 92 through the movement of a rearming lever 128. Rearming lever 128 is pivotally mounted between housing halves 4a, 4b through the engagement of pivot pins 130 engaging holes 132 formed in halves 4a, 4b. A portion 134 of lever 128 extends within cutouts 136 formed in the top portions 86 of housing halves 4a, 4b. Lever 128 includes a U-shaped interior portion 138 having a curved distal surface 140 which lies against the proximal surface 142 of drive plate 84. Lifting portion 134 of rearming lever 128 from the position of FIG. 3B to the position of FIG. 3A causes the rearming lever to pivot about pins 130 causing curved surface 140 to press against proximal surface 142 to force drive plate 84 in distal direction 118 against the biasing force of springs 94. The pivoting of rearming lever 128 also moves shield control block 114 in proximal direction 92. This is accomplished by connecting block 114 to lever 128 by a bent wire form 144. Wire form 144 includes a proximal leg 146 which engages a transverse hole 148 formed in an extension 150 on the distal side of portion 134 of lever 128. Wire form 144 also includes a distal leg 152 which passes through an axially extending slot 154 formed in shield control block 114.

With rearming lever 128 in the transverse position of FIGS. 1 and 3B, springs 94 pull on first cable segment 80, which rotates pulley 62, which pulls on second cable segment 82, thus pulling shield control block 114 in distal direction 118 and against set screw 124. See FIG. 3B. Moving rearming lever 128 to the axial position of FIG. 3A forces drive plate 84 against springs 94 and, simultaneously, lifts shield control block 114 in proximal direction 92 virtually immediately because distal leg 152 was at the distal end of slot 154 in FIG. 3B. Doing so causes safety shield 46 to move to the cutting position of FIGS. 1 and 3A.

Safety shield 46 is retained in the cutting position by the engagement of the distal end 156 of a plastic release spring 158 with safety shield 46. Release spring 158 is substantially housed within an axial slot 160 formed in blade 36 as illustrated in FIGS. 2 and 2A. A transverse bore 162, shown in FIG. 2B, opens into the proximal end of slot 160. Bore 162 is sized to permit the proximal angled end 164 of release spring 158 to be press fit into bore 162 thus retaining plastic spring 158 within axial slot 160. Release spring 158 is sized and positioned so that distal end 156 engages an axially extending slot 166 formed in inner face 58 of safety shield half 50. See FIG. 2C. Doing so keeps safety shield 46 in the cutting position of FIGS. 1 and 3A.

Returning rearming lever 128 to the transverse position of FIG. 1 disengages curved surface 140 from proximal surface 142 of drive plate 84. However, the engagement of distal end 156 of release spring 158 within slot 166 of safety shield half 50 prevents springs 94 from rotating safety shield 46. Since cable 70 is not moved by the movement of rearming lever 128 from the axially extending position of FIG. 3A to the transversely extending position of FIGS. 1 and 3B, shield control block 114 also does not move. However, distal leg 152 of wire form 144 passes from the proximal end of slat 154 towards the distal end of slot 154 formed the shield control block. (This position is not illustrated.)

Release spring 158 includes a radially extending button 168 positioned proximally of safety shield 46 and within an arcuate cutout 170 formed at distal end 34 of barrel 6. Pressing on button 168 disengages distal end 156 from slot 166 to permit springs 94 to force drive plate 84 in proximal direction 92 thus pulling on first cable segment 80 and rotating safety shield 46. The rotation of safety shield 46 pulls on cable segment 82 thus moving shield control block 114 in the direction of arrow 74 in FIG. 3B to the position of FIG. 3B. This movement of safety shield 46 is halted by the engagement of block 114 with set screw 124. Button 168 is depressed during the use of obturator 2 when the tissue through which the tip 172 of obturator 2 is passing presses against and thus depresses button 168.

As shown in FIG. 2C, more than half, and preferably more than two-thirds, of safety shield 46 is located in proximal direction 92 of shield axis 66. This configuration helps to ensure that safety shield 46 remains in essentially the cutting position of FIGS. 1 and 3A until blade 36 has at least substantially, and typically completely, cut the tissue layer being breached.

Positioning release button 168 proximally of safety shield 46, as opposed to extending from the safety shield, allows tip 172 of obturator 2 to be made with a smaller diameter than would otherwise be practical.

In use, the physician first makes a small incision with a scalpel at the point of entry. With safety shield 46 in the cutting position of FIG. 1, the tapered tip 172 of obturator 2, which is typically housed within a trocar body, not shown, is then pressed through the slit in the patient's skin, through the fatty tissue layer until tip 172 reaches the muscular fascial layer. As this is occurring, the cut tissue depresses button 168 to release distal end 156 of spring 158 from slot 166. Once cutting edge 40 of blade 36 is through the muscular fascial layer, the force exerted on safety shield 46 by the tissue become insufficient to keep safety shield 46 from rotating about 180° to the safe position of FIG. 3B. Obturator 2 can then removed from the trocar body. To reset obturator assembly 6 to the cutting position of FIG. 1, lever 128 is lifted from the position of FIGS. 1 and 3B to the position of FIG. 3A so safety shield 46 is rotated in the direction of arrow 121 to the cutting position of FIGS. 1 and 3A at which end 156 of spring 158 enters slot 166. The status of safety shield 46 can be determined by the position of indicator tab 107 within opening 14.

Figure 4:
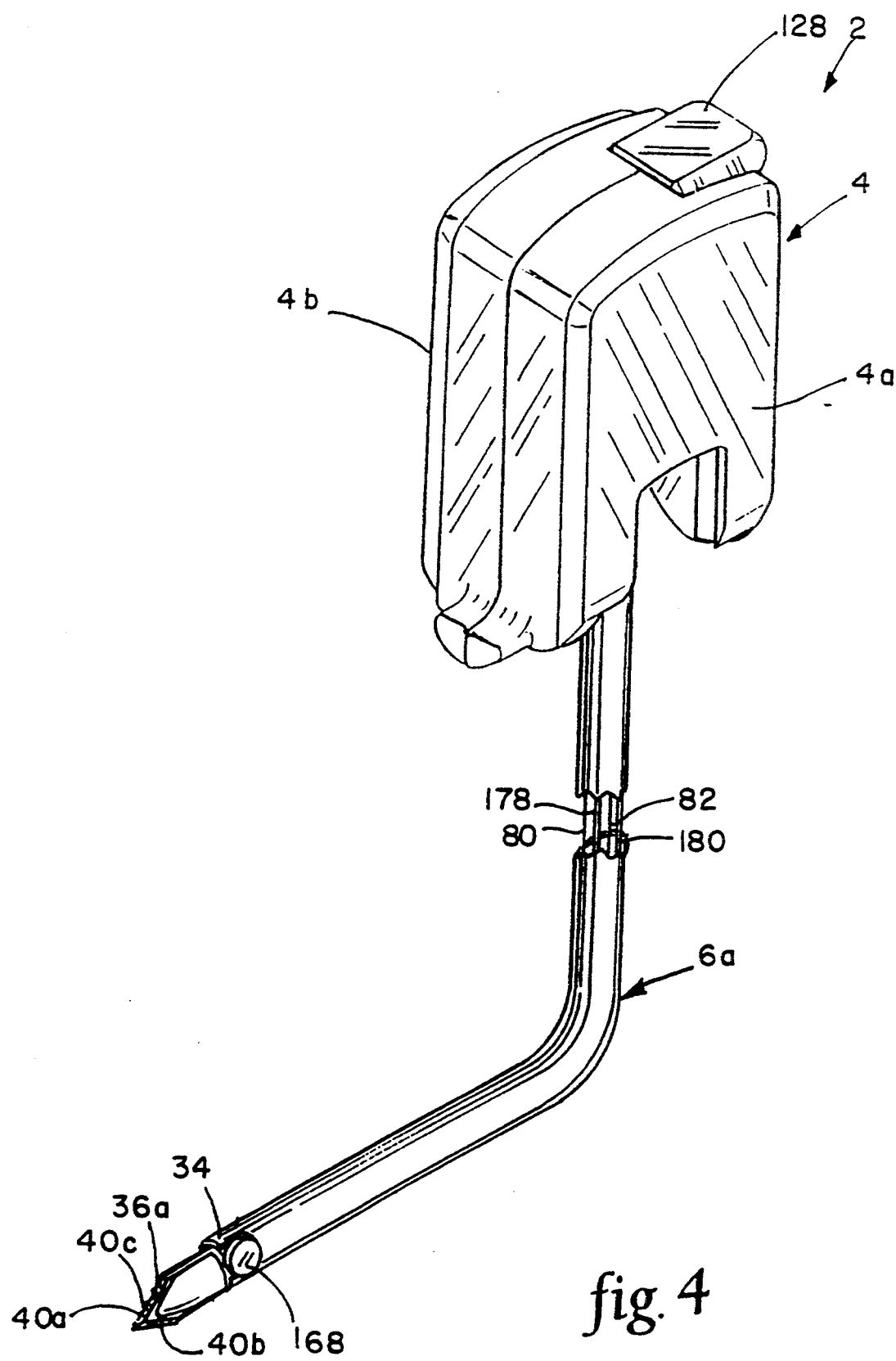
FIG. 4 is a side elevational view of an alternative embodiment of the invention, the barrel portion being flexible and having a cutting edge with smooth and serrated portions.

FIG. 4 illustrates an alternative embodiment of obturator 2. Obturator barrel 6a is flexible and can be bent into different shapes, such as the one shown in FIG. 4. Instead of being made of stainless steel as is barrel 6, barrel 6a is made of a bio-compatible material which is flexible, such as polyurethane. Blade 36 is mounted to the distal end 34 of barrel 6a. Blade 36a has a V shaped cutting edge 40a with a smooth, scalpel like portion 40b and a scalloped portion 40c. In this way cutting edge 40a can be used with great advantage with different types of tissues, some being best cut using a smooth edge while others being best cut using a scalloped or other irregular edge.

Obturator barrel 6a can be pre-bent into the desired shape prior to use. If desired, obturator barrel 6a could be made of a resilient, flexible material and could include various guiding apparatus which would allow the user to remotely guide tip 172 of obturator 2a by manipulation of guide cables 178, 180 as is conventional. Appropriate fiberoptic imaging apparatus could also be used.

FIGS. 5-8D illustrate a second preferred embodiment of the invention. Obturator 2a is illustrated with like reference numerals referring to like parts. Obturator 2a includes a housing 4' having housing halves 4'a and 4'b. Housing halves 4'a, 4'b are secured to one another using pins 10 which engage complementary pin openings 12. Housing halves 4'a, 4'b are substantially mirror images of one another. However, housing half 4'a has a small opening (not shown) in its outer face 16a, used to signal the safe/use condition of obturator 2a as discussed below. Also, housing half 4'b has a post (not shown) similar to rocker mount 260 of housing half 4'a but without the necked down portion 258.

A generally rectangular mount plate 18a is supported with housing 4' by pins 182, 183 which engage complementary holes 184 in housing halves 4'a, 4'b. Pin 182 passes completely through mount plate 18a, but also through a pair of slots 186 formed in mount plate 18a. The distal ends of a drive spring 94a and a return spring 188 are connected to the portions of pins 182 passing through slots 186 for purposes to be discussed below. Mount plate 18a also has a stepped central hole 32a through which ends 72a, 74a of drive cable segments 80a, 82a pass.

The proximal end 190 of obturator barrel 6a is press fit into a larger-diameter distal portion of opening 32a, not shown but similar to that shown in FIG. 3A. The distal end 34a of obturator barrel 6a is sized to accept blade 36a.

Blade 36a includes a blade element 192 having a cutting edge 40 and an opening 42a formed in its distal end. Blade element 192 is typically made of stainless steel. Blade 36a also includes plastic cradle elements 194, 196 configured to be mounted on opposite sides of blade element 192 and to be secured thereto. Cradle element 194 has an oblong recess 198; blade element 194 has an oblong opening 200 which substantially matches and is aligned with recess 198. Cradle element 196 has a projection 202 sized to fit snugly within opening 200 and recess 198 so to secure cradles 194, 196 on either side of blade element 192.

Cradle element 196 has a release spring arm 158a which functions like release spring 158 of FIG. 2D. Arm 158a has a button 168a which is pressed inwardly during use by the tissue being breached. Arm 158a has a safety shield engagement tab 156a at its distal end used for the same purpose as the tip 156 of release spring 158 of obturator 2, as will be discussed below. The distal end of arm 158a is positioned opposite a second opening 204 formed in blade element 192 to permit the relatively free radial movement of tab 156a.

Blade element 192 also includes pair of axially extending cable slots 206, 208 positioned along the lateral edges of blade element 192 and then inwardly to connect with opening 42a. Cable slots 206, 208 are provided to permit cable segments 80a, 82a to pass freely from opening 42a, past blade 36a and into interior 90a of obturator barrel 6a. As can be seen from the figures, blade element 192 is substantially flat and is designed so that all machining operations, with the exception of creation of cutting edge 40, can take place from one side. This substantially simplifies manufacture.

Figure 5:
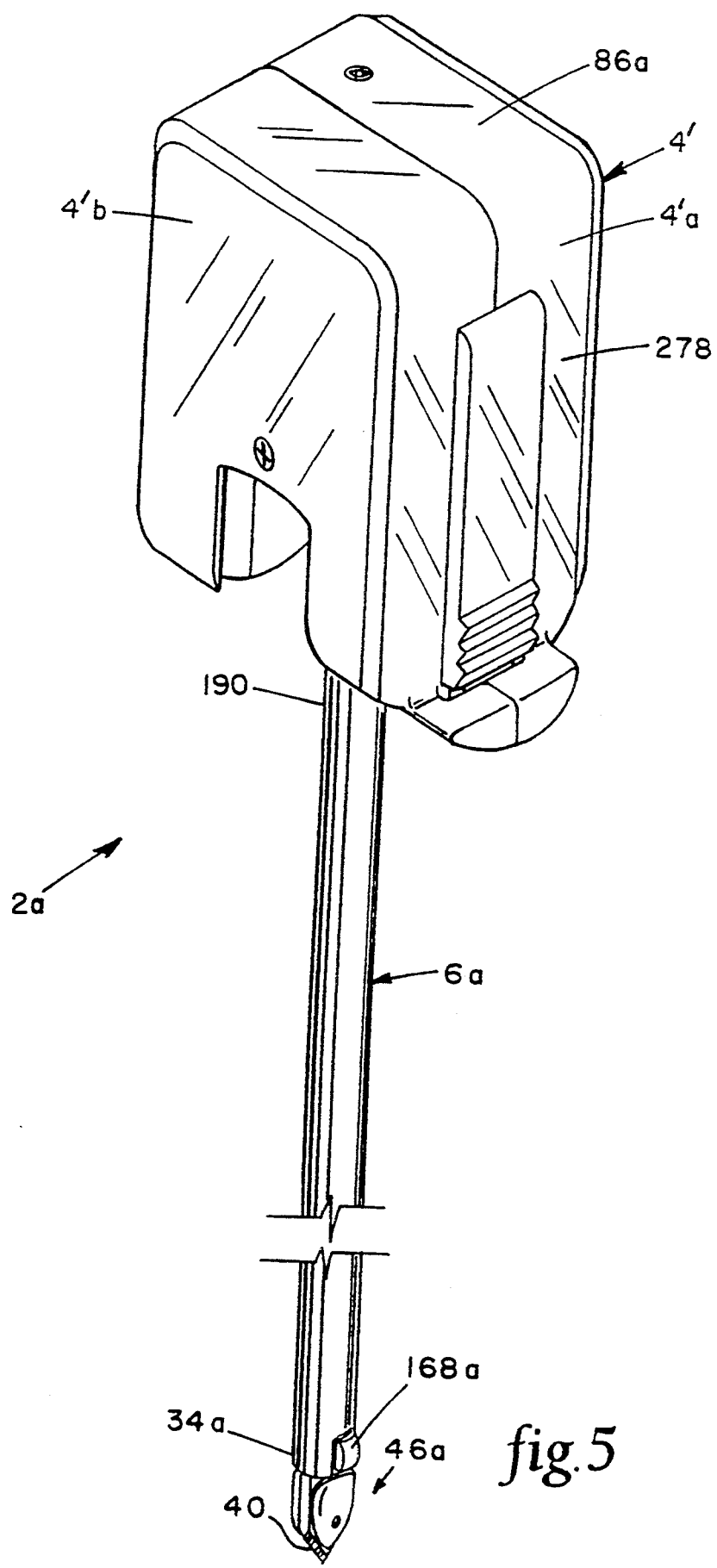
FIG. 5 is an overall isometric view of a second preferred embodiment of an obturator made according to the invention.
Figure 6:
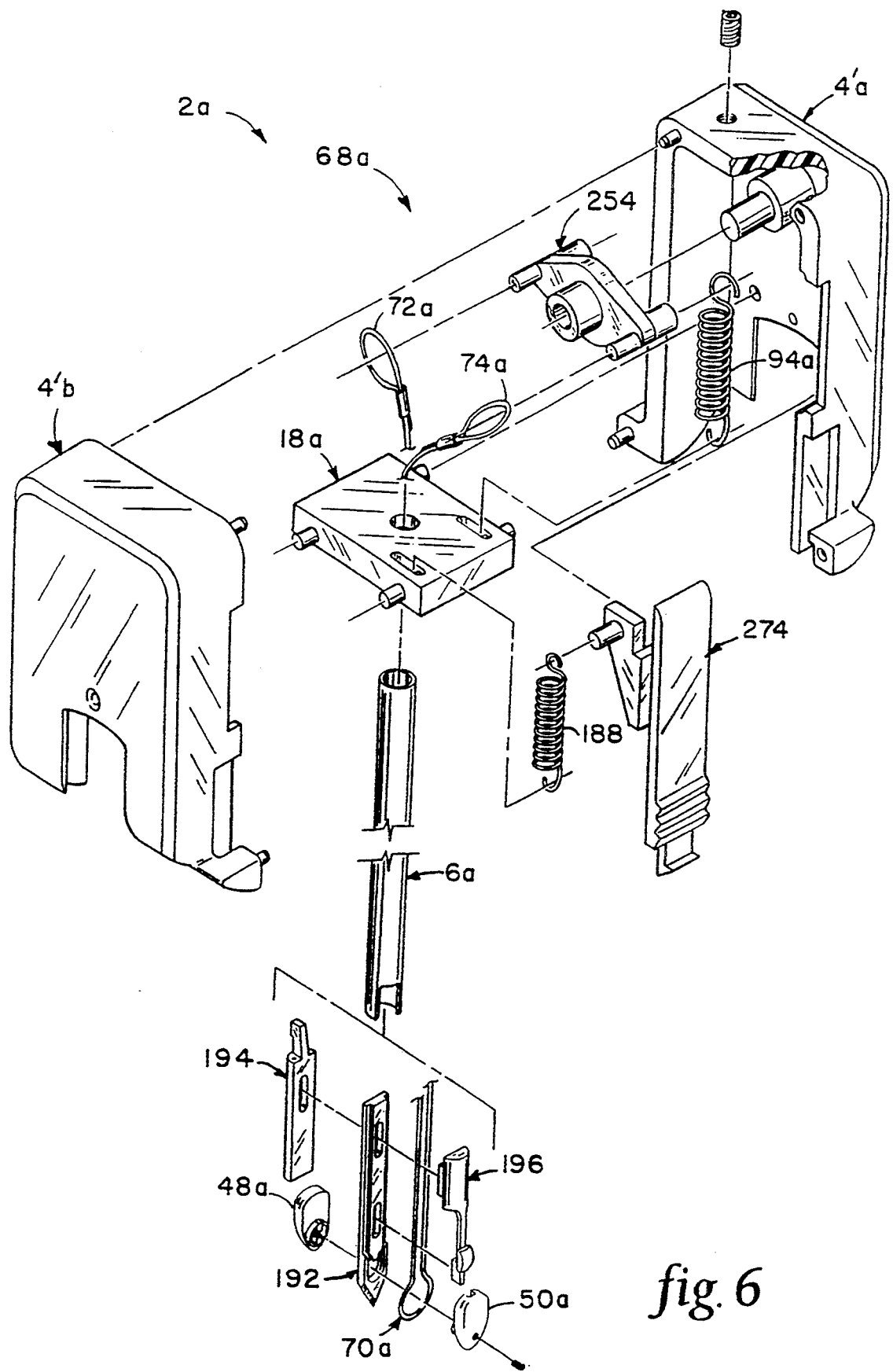
FIG. 6 is an exploded, isometric view of the obturator of FIG. 5.

Obturator barrel 6a has an opening, not shown in the figures, into which a cradle element mounting tab 212, extending from the proximal end of cradle element 194, enters when blade 36a is inserted into distal end 34a with tab 212 aligned with the opening. Outer cylindrical surfaces 214, 216 of cradle elements 194, 196 are sized to permit blade 36a to slide easily into but snugly within obturator barrel 6a until cradle element mounting tab 212, which is at the end of a resilient arm 218, engages opening 210. When this occurs, blade 36a is secured to distal end 34a of obturator barrel 6a. As shown in FIGS. 5 and 6, obturator barrel 6a has a cut-out 220 at distal end 34a sized and shaped to accept button 168a.

Figure 7:
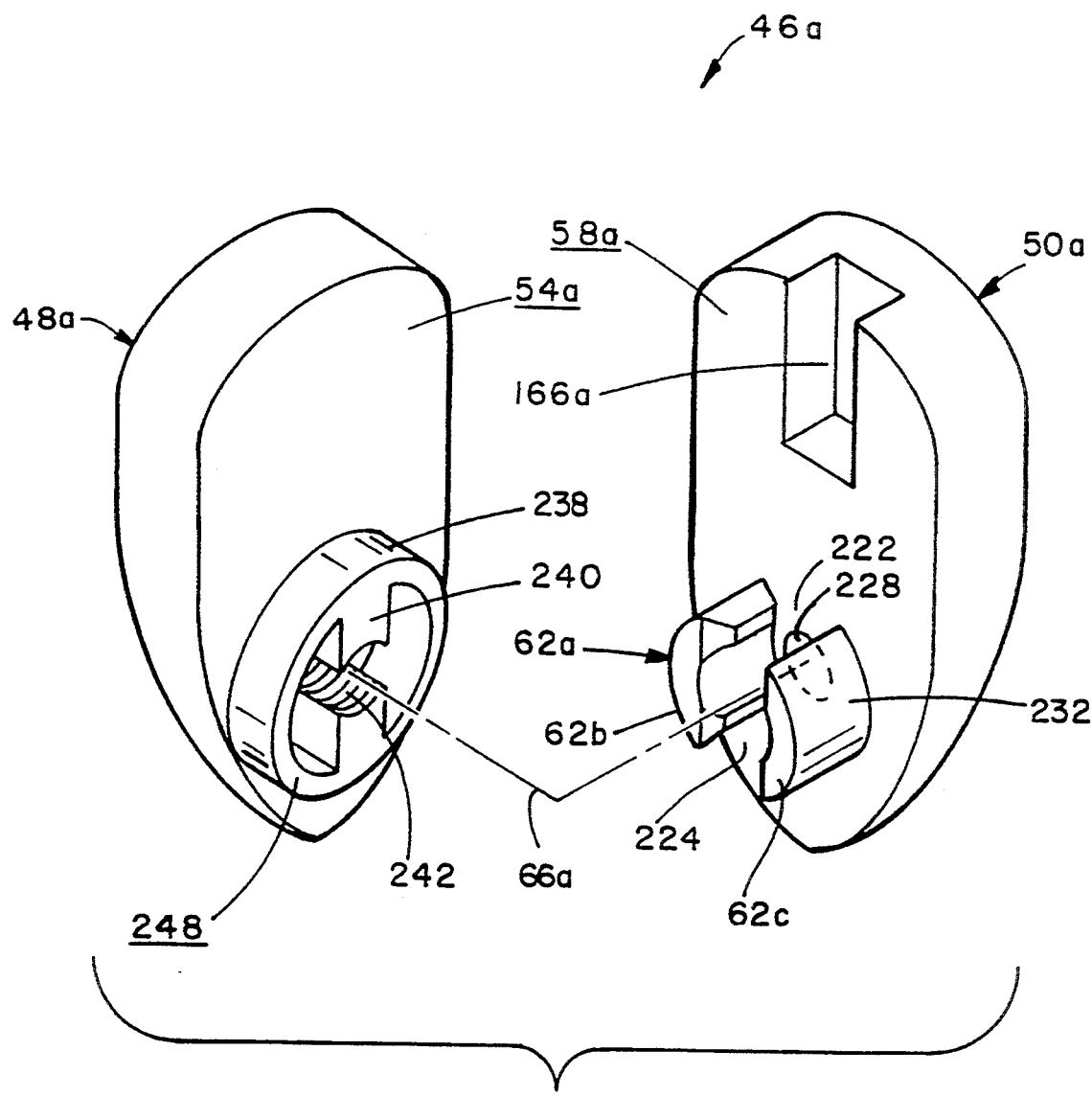
FIG. 7 is an enlarged, exploded isometric view of the safety shield of FIG. 6C.

Safety shield 46a, shown best in FIG. 7, is pivotally mounted to the blade element 192 of blade 36a. Safety shield halves 48a, 50a have projecting members extending from their inner faces 54a, 58a. Segmented pulley 62a extends from inner face 58a. Segmented pulley 62a includes pulley halves 62b, 62c separated by cut-outs 222, 224 positioned on opposite sides of axis 66a. Pulley 62a has a hollow interior sized to permit a connecting screw 226, which passes through a through hole 228 formed in shield half 50a, to pass between pulley halves 62b, 62c and define an annular open region 230 between screw 226 and pulley halves 62b, 62c. See FIGS. 8A–8D. This arrangement of pulley 62a and connecting screw 226 permits the novel securement of drive cable 70a to the pulley as shown in FIGS. 8A–8D.

Figure 8A:
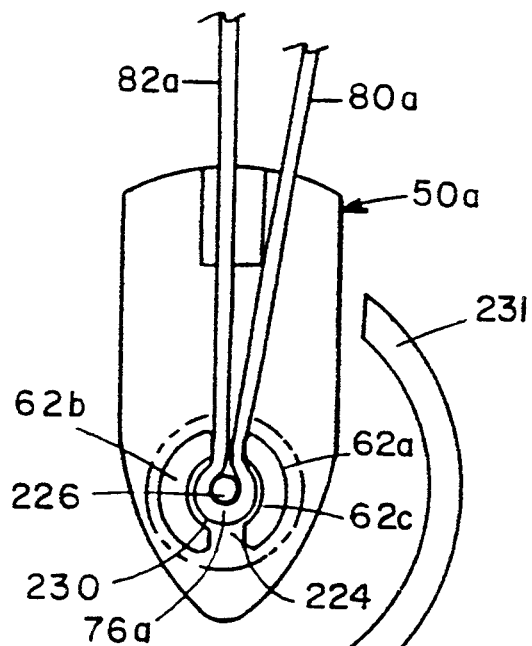
FIGS. 8A–8D are simplified schematic representations illustrating how the drive cable is mounted to and wound about the safety shield pulley.
Figure 8B:
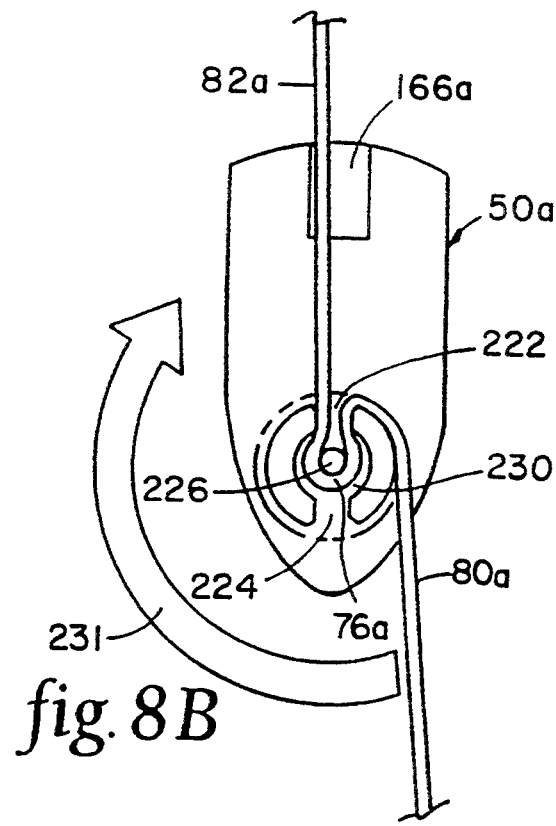
Figure 8C:
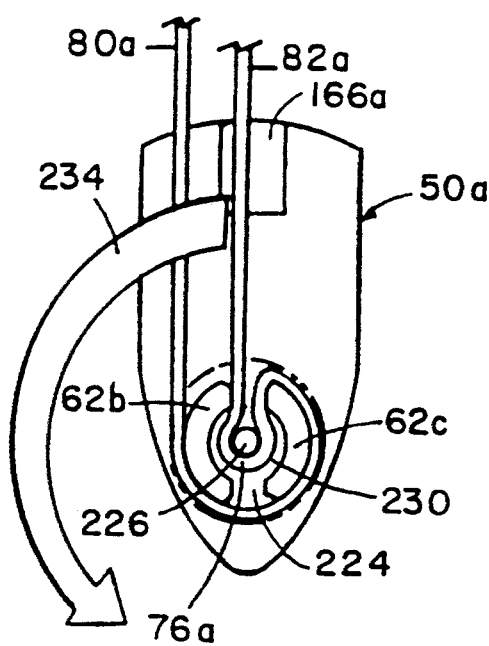
Figure 8D:
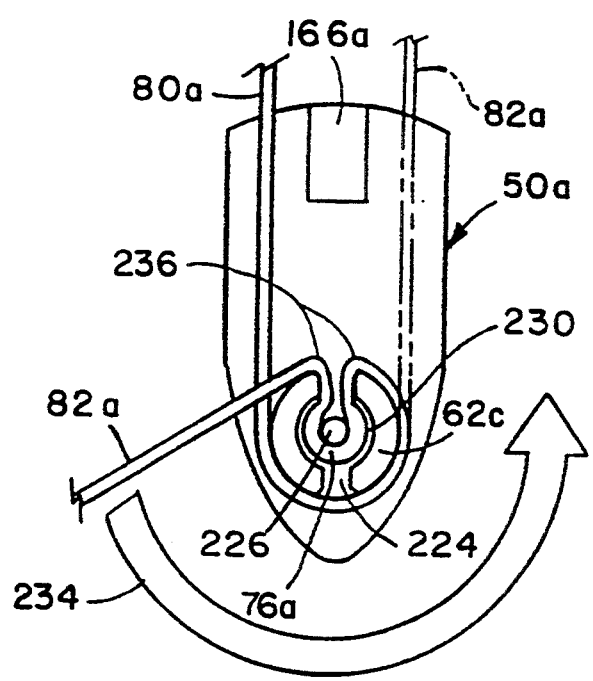

Intermediate portion 76a of drive cable 70a is preformed to the general configuration of FIG. 8A and is placed within annular open region 230 and against connecting screw 226 as shown in FIG. 8A. First cable segment 80a is then wrapped in the direction of arrow 231 around the outer drive surface 232 of pulley 62a. This causes first cable segment 80a to be wrapped around about 270° of pulley 62a as shown in FIGS. 8A–8C. Similarly, second cable segment 82a is wrapped in the opposite direction, that is the direction of arrow 234 as shown in FIGS. 8C and 8D until it assumes the dashed-line position of FIG. 8D and is also wrapped about 270° around surface 232. As is seen from FIG. 8D, drive cable 70a has a pair of very sharp bend points 236 near intermediate portion 76a and adjacent cut-out 222. It has been found that sharp bends in drive cable 70a causes work hardening of the drive cable material at points 236 so that subsequent flexing of the drive cable during use at these points of high bending can cause the drive cable to fail prematurely. With the present invention, drive cable 70 is not flexed at points 236 during use since safety shield 46a only rotates 180° during its movement between safe and cutting positions while each cable segment 80a, 82a is wrapped around pulley 62a about 270° when safety shield 46a is in the cutting position.

In the embodiment showed in FIGS. 8A–8D, cut-outs 222, 224 are generally aligned with the longitudinal axis of obturator 2a. If desired, cut-outs 222, 224 could be rotated 90° in a clockwise direction from the position of FIG. 8A. Doing so would cause first and second cable segments 80a, 82a to be wrapped around pulley 62a about 360° and 180° respectively with safety shield 46a in the cutting position of FIG. 8D. This is possible because movement of safety shield 46a from the cutting position of FIG. 8D 180° in a counterclockwise direction causes first cable segment 80a to unwrap about 180° and second cable segment 82a to wrap about 180°. Reversing this, that is pulling on cable segment 82a to rotate segmented shield 46a in the direction of arrow 231 to return the safety shield to the cutting position of FIG. 8D, causes the opposite effect. With such an orientation of cutouts 222, 224, the cable segments would always be wrapped at least about 180° around pulley 62a.

Safety shield half 48a has an integrally formed support ring 238 sized to rotate within opening 42a formed in blade element 292. Support ring 238 includes a pair of keys 240 sized to fit within cut-outs 222,224. A threaded bore 242 is formed along axis 66a within support ring 238 for threaded engagement with connecting screw 226. Inner surface 54a of safety shield half 48a abuts surface 244 of blade element 192 while surface 58a abuts the opposite surface 246 of blade element 192. Since pulley 62a extends outwardly away from surface 58a a greater distance than support ring 238 extends from inner surface 54a, an annular gap, equal to about the depth of grooves 206, 208, is formed by the outer face 248 of support ring 238, inner surface 58a and drive surface 232 of pulley 62a. This provides sufficient room for the wrapping of drive cable 70a without binding.

Figure 6A:
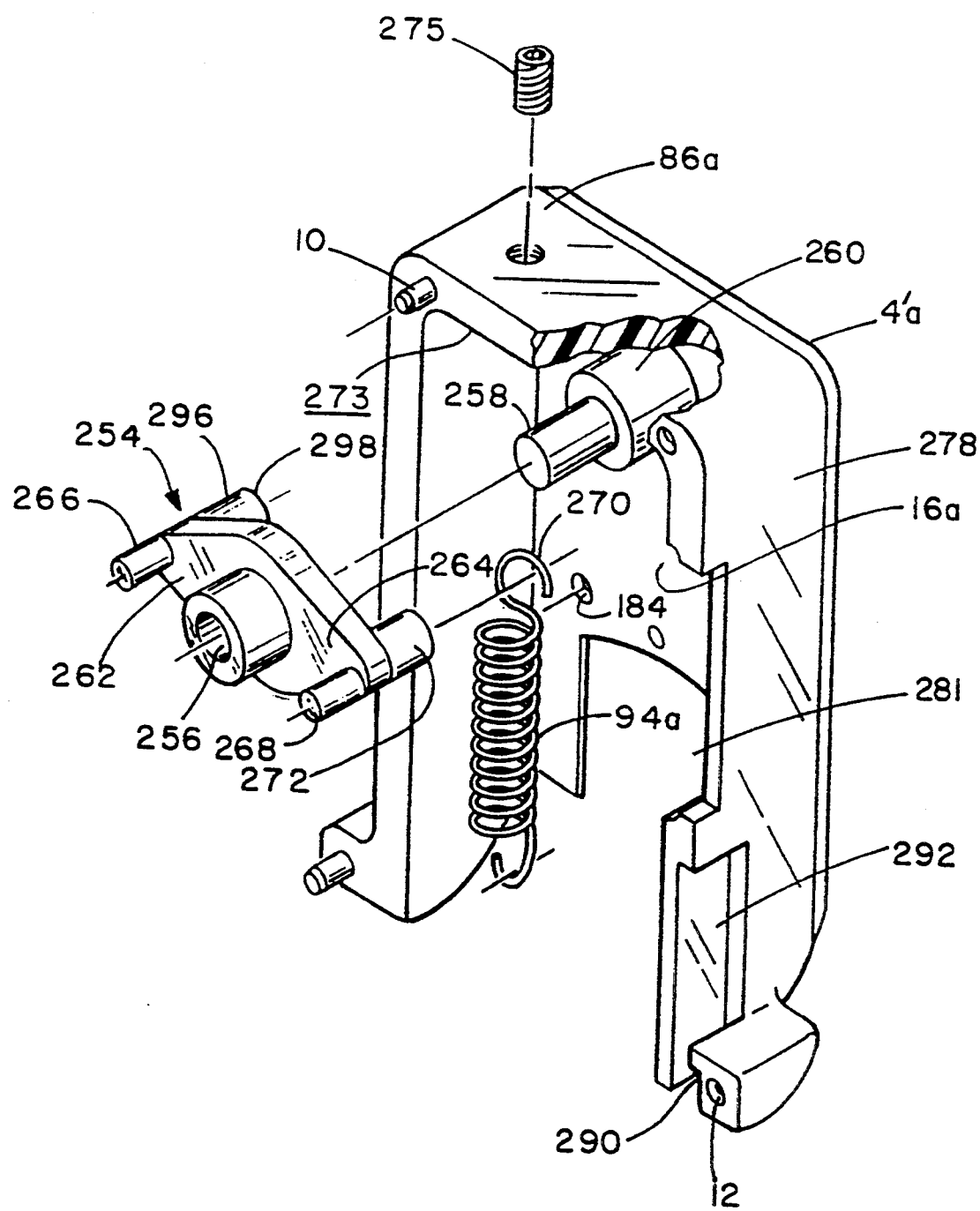
FIGS. 6A–6C are enlarged views of groupings of components of the obturator of FIG. 6.
Figure 6B:
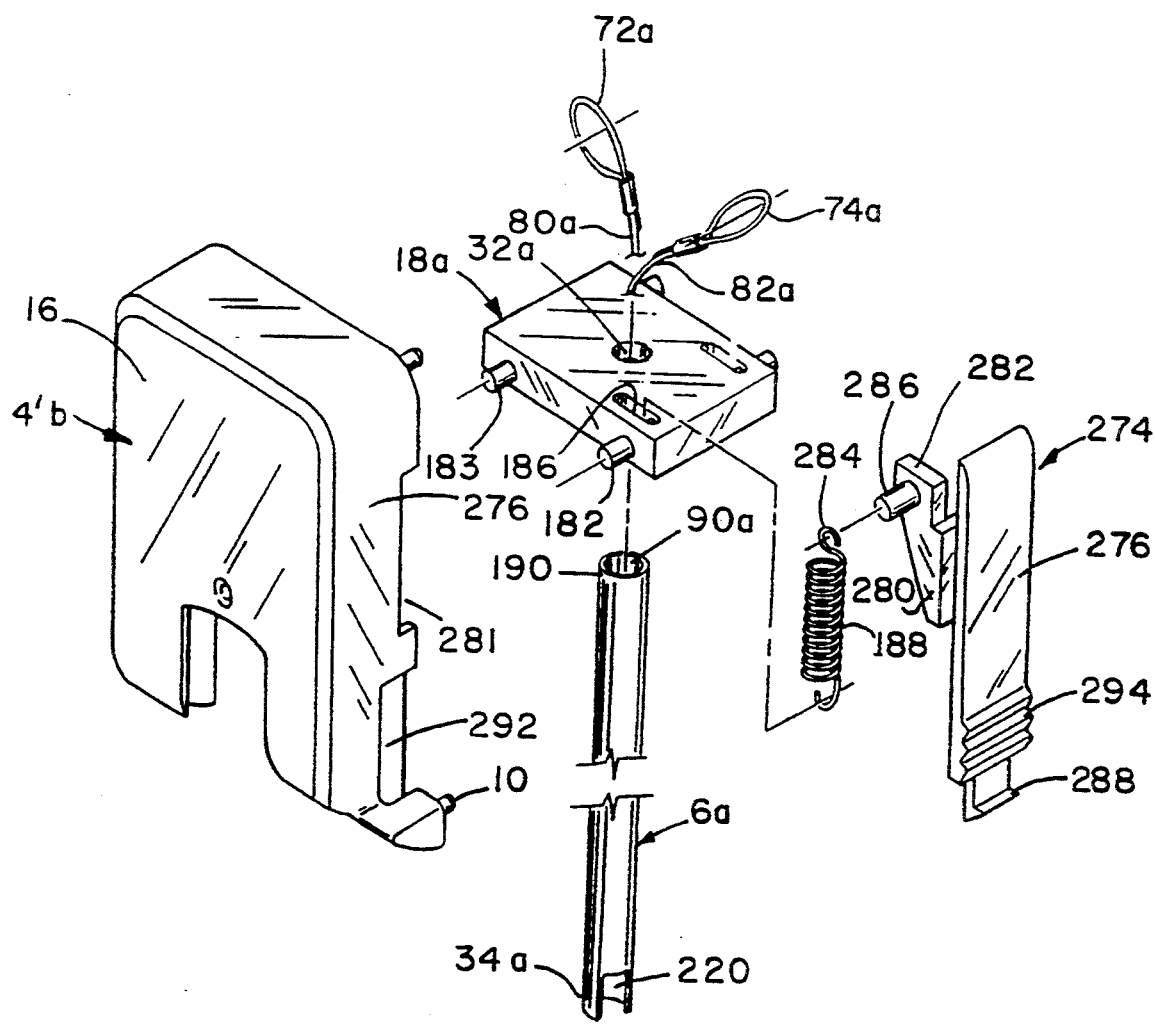
Figure 6C:
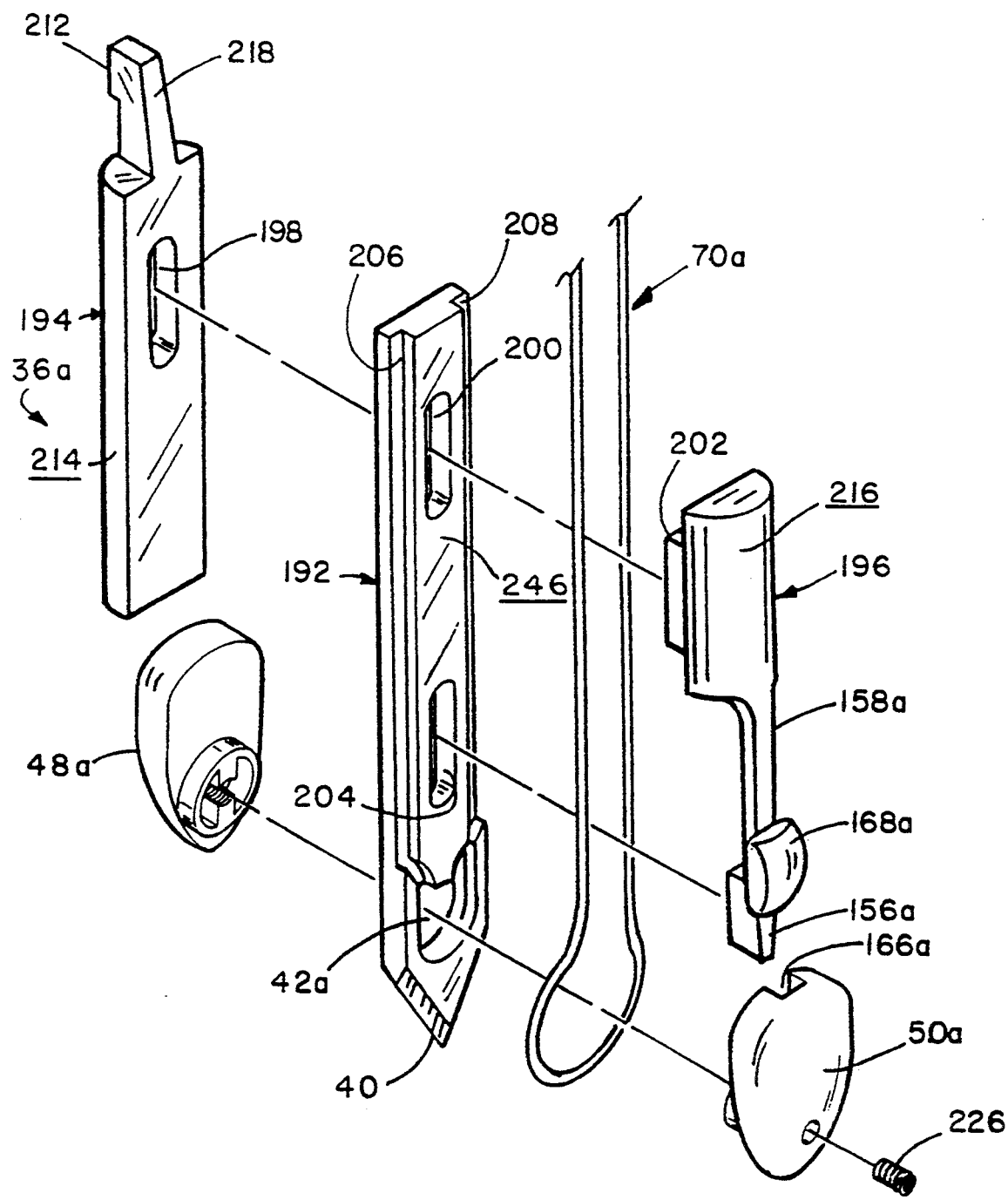

Turning now to FIGS. 6–6B, safety shield driving assembly 68a will be described. Driving assembly 68a is relatively simple and rugged in construction. Safety shield drive assembly 68a includes a rocker 254 having a central bore 256 used to mount the rocker onto the necked down portion 258 of a rocker mount 260 extending from housing half 4'a. Rocker 54 includes a drive arm 262 and a return arm 264 extending radially away from and on either side of central bore 256. Drive arm 262 has a drive pin 266 extending from its distal end over which end 72a of drive cable 80a is mounted. Similarly, return arm 264 has a return pin 268 extending from its distal end and over which end 74a of return cable 82a is mounted.

Rocker 254 is normally biased to pivot in a clockwise direction in FIG. 6A, so that drive pin 266 normally pulls on drive cable segment 80a, thus placing the drive cable segment in tension. This biasing is achieved by the engagement of the proximal end 270 of drive spring 94a with a drive spring pin 272 extending from the distal end of return arm 264 opposite return pin 268. The clockwise pivotal movement of rocker 254 is limited by the engagement of drive arm 262 with internal upper surface 273 of housing half 4'a. The final position of rocker 254 can be adjusted through the use of, for example, a set screw 275 advancing through top portion 86a of housing half 4'a. Such adjustment would be used to adjust the final position of safety shield 46a in the safe position, corresponding to the safe position of FIG. 3B.

Rocker 254 is moved against the bias of drive spring 94a from the reset position, corresponding to safe position of safety shield 46a, to the drive position, corresponding to the cutting position of the safety shield, by a rearming slider 274. Rearming slider 274 includes a main body 276 positioned against an outer sidewall surface 278 of housing 4'. Rearming slider 274 includes a rearming arm 280 extending into the interior of housing 4' through cut-out 281 formed in housing 4'. Arm 280 has a proximally facing surface 282 positioned beneath return arm 264 to permit the rocker 254 to be rotated from the reset position to the drive position by moving rearming slider 274 proximally causing surface 282 to engage return arm 264 thus pivoting rocker 254. When this has been achieved, safety shield 46a is temporarily locked in position by the engagement of safety shield engagement tab 256a with slot 166a formed in inner face 58a of shield half 50a.

When the user releases the arming slider 274, return spring 188, whose proximal end 284 is mounted to a pin 286 extending laterally from rearming arm 280, biases rearming slider 274 in a distal direction back to its first position. In the first position, a resilient catch 288 extending from the distal end of main body 276 of rearming slider 274 engages a catch ledge 290 formed in housing 4' opposite a recess 292 formed in housing 4'. This keeps rearming slider 274 from inadvertently moving from its first position. However, when it is desired to rotate rocker 254 from its reset position to its drive position, the user merely presses ridged surface 294 formed on body 276 to disengage catch 288 from catch ledge 290 and permit rearming slider 274 to move in a proximal direction against the bias of return spring 188 and rotate rocker 254 against the bias of drive spring 94a.

Rocker 254 includes an indicator pin 296 having an outer face 298 preferably painted red. Outer face 298 is positioned opposite a view port (not shown) formed in housing half 4'a when safety shield 46a is in the cutting position. This allows a user to quickly determine the status of safety shield 46a when the safety shield is not visible.

The present invention is made from conventional biocompatible materials. For example, blade 36, blade element 192, springs 94, 188, obturator barrel 6, cable 70, wire form 144, guide pin 110 and screws 124, 226 are preferably made from stainless steel. The remaining parts can be made of polycarbonate or other appropriate materials.

Obturator 2 may be used with a variety of trocar housings, such as made by Origin Med Systems, Inc. of Menlo Park, Calif. Obturator 2 can also be used with trocar housings disclosed in various patents and patent applications, such as Ser. Nos. 08/015,170; 08/019,548; 08/031,174; 08/033,315; and 08/039,310.

Other modifications and variations can be made to the disclosed embodiments without departing from the subject of the invention as defined in the following claims. For example, cutting edge 40 could be other than straight. Pulley 62 need not be round. Second cable segment 82 could be connected directly to rearming lever 128; however, the preferred embodiment permits the easy adjustment of the limit of travel of safety shield 46 through set screw 124. Also, rearming lever 128 could be constructed so as not to touch drive plate 84 but only pull on second cable segment 82 to reset safety shield 46 to the cutting position. Drive cable 70 could be made from two separate lengths of cable, each secured to pulley 62. Cradle elements 194, 196 could be made as a single part.

What is claimed is:

1. An obturator, usable as part of a trocar to provide an opening through a tissue layer, comprising:
   an elongate obturator body having proximal and distal ends;
   a cutting element at the distal end;
   a safety shield pivotally mounted to the distal end and adjacent the cutting element, the safety shield being pivotal between a cutting position, with the cutting element exposed to the tissue layer, and a safe position, with the safety shield shielding the cutting element; and
   means for automatically rotating the safety shield from the cutting position to the safe position upon passage of the cutting element at least substantially through the tissue layer, the safety shield rotating means including means, operable from the proximal end, for returning the safety shield from the safe position to the cutting portion.

2. The obturator of claim 1 wherein the cutting element includes a flat blade.

3. The obturator of claim 1 wherein the cutting element includes a cutting edge having first and second portions, the first portion including a smooth cutting edge and the second portion including an irregular cutting edge.

4. The obturator of claim 3 wherein the irregular cutting edge is a serrated cutting edge.

5. The obturator of claim 3 wherein the first and second portions define a V-shaped cutting edge.

6. The obturator of claim 1 wherein the obturator body includes an obturator barrel.

7. The obturator of claim 6 wherein the cutting element includes an elongate, generally flat, blade element and a cradle piece mounted to the blade element, the cradle piece and blade element therewith sized to be partially housed within the obturator barrel, the cradle piece being configured to maintain the safety shield in the cutting position until the cradle piece is engaged by the tissue layer.

8. The obturator of claim 7 wherein the cradle piece includes first and second cradle elements secured to one another on opposite sides of the blade element.

9. The obturator of claim 8 wherein the blade element includes an opening formed therethrough, the second cradle element includes a recess formed therein, and the first cradle element includes a protrusion sized to pass through the opening in the blade element and into the recess in the second cradle element.

10. The obturator of claim 7 wherein the obturator barrel includes a cradle catch and the cradle element includes a cradle element mounting tab engageable with the cradle catch so to maintain the cutting element mounted to the obturator barrel.

11. The obturator of claim 10 wherein the cradle catch is defined by an opening formed in the obturator barrel.

12. The obturator of claim 7 wherein the safety shield includes a safety shield-catch and the cradle piece includes a resilient arm having a safety shield engagement catch normally biased towards engagement with safety shield-catch when the safety shield is in the cutting position.

13. The obturator of claim 6 wherein the obturator barrel is a rigid, straight barrel.

14. The obturator of claim 6 wherein the obturator barrel is a flexible barrel so that the barrel can be bent for use.

15. The obturator of claim 14 wherein the flexible obturator barrel is a steerable flexible obturator barrel.

16. An obturator, usable as part of a trocar to provide an opening through a tissue layer, comprising:
an elongate obturator body having proximal and distal ends and a body axis;
a cutting element at the distal end;
a safety shield pivotally mounted to the distal end and adjacent the cutting element, the safety shield being pivotal between a cutting position, with the cutting element exposed to the tissue layer, and a safe position, with the safety shield shielding the cutting element; and
means for automatically rotating the safety shield around a shield axis from the cutting position to the safe position upon passage of the cutting element at least substantially through the tissue layer, the safety shield rotating means including means, operable from the proximal end, for returning the safety shield from the safe position to the cutting portion, the shield axis being oriented generally perpendicular to the body axis.

17. The obturator of claim 16 wherein the flat blade includes a V-shaped cutting edge.

18. The obturator of claim 17 wherein the shield axis is located adjacent a proximal portion of the V-shaped cutting edge.

19. The obturator of claim 16 wherein the safety shield is configured so that when the safety shield is in the cutting position, at least ½ of the safety shield is proximal of the shield axis.

20. The obturator of claim 16 wherein the safety shield is configured so that when the safety shield is in the cutting position at least ⅔ of the safety shield is proximal of the shield axis.

21. An obturator, usable as part of a trocar to provide an opening through a tissue layer, comprising:
an elongate obturator body having proximal and distal ends and an obturator barrel;
a cutting element at the distal end, the cutting element including an elongate, generally flat, blade element and a cradle piece mounted to the blade element, the cradle piece and the blade element therewith sized to be partially housed within the obturator barrel;
a safety shield pivotally mounted to the distal end and adjacent the cutting element, the safety shield being pivotal between a cutting position, with the cutting element exposed to the tissue layer, add a safe position, with the safety shield shielding the cutting element; and
means for automatically rotating the safety shield from the cutting position to the safe position upon passage of the cutting element at least substantially through the tissue layer, the safety shield rotating means including means, operable from the proximal end, for returning the safety shield from the safe position to the cutting portion and a drive cable operably coupled to the safety shield, the drive cable including first and second drive cable segments extending through the obturator barrel.

22. The obturator of claim 21 wherein the cradle piece and the blade element define a passageway for passage of the drive cable segments along the cutting element.

23. The obturator of claim 22 wherein the passageway is partially formed by first and second cable grooves formed in a first side of the blade element.

24. The obturator of claim 21 wherein the safety shield rotating means includes a drive cable operably coupled to the safety shield.

25. The obturator of claim 24 wherein the safety shield rotates a first rotary distance when moving between the cutting and safe positions.

26. The obturator of claim 25 wherein the safety shield includes a pulley and the cable includes drive and return cable segments.

27. The obturator of claim 26 wherein the drive and return cable segments are wrapped about the pulley second and third rotary distances, each of said second and third rotary distances being sufficient so that neither of the drive or return cable segments are substantially fully unwound from the pulley during movement of the safety shield between the safe and cutting positions.

28. The obturator of claim 27 wherein the second and third rotary distances are each about 270° when the safety shield is in the cutting position and the first rotary distance is about 180°.

29. The obturator of claim 26 wherein the pulley includes an outer surface around which the cable is wrapped, a centrally positioned element surrounded by an annular open region and a radially extending cut-out connecting the annular open region with the outer surface.

30. The obturator of claim 29 wherein the drive and return cable segments are joined at a common region, the common region lying within the annular open region and against the centrally positioned element with the drive and return cable segments extending through the cut-out and then around the outer surface in opposite rotary directions.

31. An obturator, usable as part of a trocar to provide an opening through a tissue layer, comprising:

an elongate obturator body having proximal and distal ends;

a cutting element at the distal end;

a safety shield pivotally mounted to the distal end and adjacent the cutting element, the safety shield being pivotal between a cutting position, with the cutting element exposed to the tissue layer, and a safe position, with the safety shield shielding the cutting element; and means for automatically rotating the safety shield from the cutting position to the safe position upon passage of the cutting element at least substantially through the tissue Layer, the safety shield rotating means including means, operable from the proximal end, for returning the safety shield from the safe position to the cutting portion and a shield driver biasing the safety shield in a rotary direction from the cutting position to the safe position.

32. The obturator of claim 31 wherein the shield driver includes a rocker pivotally mounted to the proximal end of the body to pivot between a drive position, corresponding to the cutting position of the safety shield, and a reset position, corresponding to the safe position of the safety shield.

33. The obturator of claim 32 wherein the rocker includes a pivot axis and drive and reset arms on opposite sides of the pivot axis.

34. The obturator of claim 33 wherein the shield driver includes a drive spring biasing the rocker towards the drive position.

35. The obturator of claim 31 wherein the shield driver includes an indicator providing a user with an indication of whether the safety shield is in the cutting position or the safe position.

36. The obturator of claim 31 wherein the safety shield rotating means includes a safety shield release element at the distal end of the obturator assembly positioned to be engaged by the tissue layer after the cutting element has at least partially cut the tissue layer.

37. The obturator of claim 36 wherein the safety shield release element is operable between a safety shield engaged condition, at which the safety shield is maintainable in the cutting position against the force of the shield driver, and a safety shield released position, at which the safety shield is released to be rotatable by the shield driver from the cutting position to the safe position, the safety shield release element being movable to the safety shield released position when said safety shield release element has been engaged by said tissue.

38. An obturator, usable as part of a trocar to provide an opening through a tissue layer, comprising:

an elongate obturator body having proximal and distal ends;

a cutting element at the distal end;

a safety shield pivotally mounted to the distal end and adjacent the cutting element, the safety shield being pivotal between a cutting position, with the cutting element exposed to the tissue layer, and a safe position, with the safety shield shielding the cutting element; and means for automatically rotating the safety shield from the cutting position to the safe position upon passage of the cutting element at least substantially through the tissue layer, the safety shield rotating means including:

means, operable from the proximal end, for returning the safety shield from the safe position to the cutting portion; and a shield driver biasing the safety shield in a rotary direction from the cutting position to the safe position, the shield driver including a rocker pivotally mounted to the proximal end of the body to pivot between a drive position, corresponding to the cutting position of the safety shield, and a reset position, corresponding to the safe position of the safety shield, the rocker including a pivot axis and drive and reset arms on opposite sides of the pivot axis, a drive spring biasing the rocker towards the drive position and a cable, the cable including drive and reset cable ends secured to the drive and reset arms, respectively.

39. The obturator of claim 38 wherein the drive spring connects the drive arm to the body.

40. The obturator of claim 38 further comprising a rearming member movably mounted to the proximal end of the body for movement between first and second orientations, the rearming member having a part which engages the rocker when the reset member is moved from the first orientation to the second orientation so to move the rocker from the reset position to the drive position.

41. The obturator of claim 40 further comprising means for biasing the rearming member towards the first orientation.

42. The obturator of claim 38 wherein the safety shield includes a pulley and the shield driver includes a drive spring and a drive cable, the drive cable operably coupling the drive spring and the pulley.

43. The obturator of claim 42 wherein the drive cable has first and second drive cable segments each having proximal and distal ends, the distal ends connected to the pulley, the proximal end of the first cable segment coupled to the drive spring by a drive spring coupling element whereby the drive spring provides a tension force on the first cable segment to tend to pivot the safety shield towards the safe position.

44. The obturator of claim 43 wherein the proximal end of the second cable segment is secured to a shield control element movable between first and second positions.

45. The obturator of claim 44 wherein the safety shield returning means includes a rearming assembly operable to deflect the drive spring coupling device thereby reducing tension on the first cable segment and to move the shield control element from its first position to its second position thereby pulling on the second cable segment and moving the safety shield from its cutting position to its safe position.

46. The obturator of claim 45 wherein the rearming assembly includes a pivotal rearming lever connected to the shield control element by a wire form element.

47. The obturator of claim 46 wherein the shield control element includes a slot within which a portion of the wire form element engages.

48. The obturator of claim 43 wherein the release element is positioned a distance proximally of the cutting element.

49. An improved obturator of the type used to provide an opening through a tissue layer, having proximal and distal ends and a cutting element at the distal end, the improvement comprising:
- a safety shield pivotally mounted to the distal end and adjacent the cutting element, the safety shield being pivotal between a cutting position, with the cutting element exposed to the tissue layer, and a safe position, with the safety shield shielding the cutting element; and
- means for automatically rotating the safety shield from the cutting position to the safe position upon passage of the cutting element at least substantially through the tissue layer, the safety shield rotating means including means, at the proximal end, for returning the safety shield from the safe position to the cutting position.

50. An obturator, usable as part of a trocar to provide an opening through a tissue layer, comprising:
- an elongate obturator body having proximal and distal ends;
- a cutting element at the distal end;
- a safety shield pivotally mounted to the distal end and adjacent the cutting element, the safety shield being pivotal between a cutting position, with the cutting element exposed to the tissue layer, and a safe position, with the safety shield shielding the cutting element;
- the safety shield being configured so that when the safety shield is in the cutting position at least $\frac{2}{3}$ of the safety shield is proximal of the shield axis;
- means for automatically rotating the safety shield from the cutting position to the safe position upon passage of the cutting element at least substantially through the tissue layer;
- the safety shield rotating means including a shield driver biasing the safety shield in a rotary direction from the cutting position to the safe position, the safety shield including a pulley and the shield driver including a drive spring and a drive cable, the drive cable coupling the drive spring and the pulley;
- the drive cable having first and second drive cable segments each having proximal and distal ends, the distal ends connected to the pulley, the proximal end of the first cable segment coupled to the drive spring by a drive spring coupling element whereby the drive spring provides a tension force on the first cable segment to tend to pivot the safety shield towards the safe position;
- the safety shield rotating means including a safety shield release button at the distal end of the obturator assembly positioned to be engaged by the tissue layer after the cutting element has at least partially cut the tissue layer, the safety shield release button being movable between a safety shield engaged condition, at which the safety shield is maintainable in the cutting position against the shield driver, and a safety shield released position, at which the safety shield is released to be rotatable by the shield driver from the cutting position to the safe position, the safety shield release button being movable to the safety shield released position when said safety shield release button has been depressed by said tissue;
- the safety shield rotating means including means, operable from the proximal end, for returning the safety shield from the safe position to the cutting position; and
- the safety shield returning means including:
  - a shield control element movable between first and second positions and secured to the proximal end of the second cable segment; and
  - a rearming lever connected to the shield control element and operable to deflect the drive spring coupling device thereby reducing tension on the first cable segment and to move the shield control element from its first position to its second position thereby pulling on the second cable segment and moving the safety shield from its cutting position to its safe position.

51. An obturator, usable as part of a trocar to provide an opening through a tissue layer, comprising:
- an elongate obturator body having proximal and distal ends;
- a cutting element at the distal end;
- a safety shield pivotally mounted to the distal end and adjacent the cutting element, the safety shield being pivotal between a cutting position, with the cutting element exposed to the tissue layer, and a safe position, with the safety shield shielding the cutting element;
- the safety shield being configured so that when the safety shield is in the cutting position at least $\frac{2}{3}$ of the safety shield is proximal of the shield axis;
- means for automatically rotating the safety shield from the cutting position to the safe position upon passage of the cutting element at least substantially through the tissue layer;
- the safety shield rotating means including a shield driver biasing the safety shield in a rotary direction from the cutting position to the safe position, the safety shield including a pulley and the shield driver including a drive spring and a drive cable;
- the drive cable having first and second drive cable segments each having proximal and distal ends, the distal ends connected to the pulley;
- a pivotal rocker mounted to the proximal end of the body for pivotal movement between drive and reset positions, the pivotal rocker having first and second arms, the proximal ends of the first and second cable segments connected to the first and second arms, the drive spring coupling the body and the rocker and biasing the rocker to its reset position, whereby the drive spring provides a tension force on the first cable segment through the rocker to tend to pivot the safety shield towards the safe position;
- the safety shield rotating means including a safety shield release button at the distal end of the obturator assembly positioned to be engaged by the tissue layer after the cutting element has at least partially cut the tissue layer, the safety shield release button being movable between a safety shield engaged condition, at which the safety shield is maintainable in the cutting position against the shield driver, and a safety shield released position, at which the safety shield is released to be rotatable by the shield driver from the cutting position to the safe position, the safety shield release button being movable to the safety shield released position when said safety shield release button has been depressed by said tissue;

the safety shield rotating means including means, operable from the proximal end, for returning the safety shield from the safe position to the cutting position, the safety shield returning means including a rearming element mounted to the proximal end of the body for movement between first and second positions, said rearming element, when moved from its first position to its second position, engaging the rocker so to move the rocker from its reset position to its drive position so to pull on the second cable segment and move the safety shield from its cutting position to its safe position.

* * * * *